(12) United States Patent
Yunker

(10) Patent No.: US 7,374,337 B2
(45) Date of Patent: May 20, 2008

(54) RELEASABLY INTERCONNECTED CT AND SPECT SCANNERS

(75) Inventor: David A. Yunker, Cicero, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/270,291

(22) Filed: Nov. 9, 2005

(65) Prior Publication Data

US 2006/0285647 A1 Dec. 21, 2006

(51) Int. Cl.
*H05G 1/02* (2006.01)
*H05G 1/60* (2006.01)
*G01T 1/161* (2006.01)
*G01T 1/166* (2006.01)

(52) U.S. Cl. ............... 378/198; 378/4; 378/197; 250/363.02; 250/363.04; 250/363.05; 600/407; 600/425

(58) Field of Classification Search ............... 378/4, 378/10, 19, 20, 196, 197, 198; 250/363.02, 250/363.03, 363.04, 363.05; 600/407, 425
See application file for complete search history.

(56) References Cited

U.S. PATENT DOCUMENTS 5,391,877 A * 2/1995 Marks ............... 250/363.04
6,490,476 B1 * 12/2002 Townsend et al. ........... 600/427
6,700,949 B2 * 3/2004 Susami et al. ................ 378/19
6,754,519 B1 * 6/2004 Hefetz et al. ............... 600/407
6,754,520 B2 * 6/2004 DeSilets et al. ............ 600/415
6,831,961 B1 * 12/2004 Tybinkowski et al. ......... 378/4
6,961,606 B2 * 11/2005 DeSilets et al. ............ 600/415
7,020,233 B1 * 3/2006 Tybinkowski et al. ......... 378/4
7,154,096 B2 * 12/2006 Amano ................... 250/363.03
7,162,004 B2 * 1/2007 Inoue et al. ................... 378/4

* cited by examiner

*Primary Examiner*—Allen C. Ho

(57) ABSTRACT

Arrangement for taking a CT scan and a SPECT scan of a patient in a single-pass diagnostic procedure. A SPECT scanner and a CT scanner are included. The SPECT scanner is mounted on a SPECT gantry and the CT scanner is mounted on a CT gantry. The SPECT and CT gantries are moveable with respect to one another between a mated operating configuration and a separated maintenance configuration. A pair of receiving brackets is fixedly mounted on the SPECT gantry. A pair of self-locating brackets is fixedly mounted on the CT gantry. Each of the pair of self-locating brackets is configured for assuming a prescribed position relative to a respective one of the pair of receiving brackets when in snug abutment together. A floating connection interconnects the CT scanner with the pair of self-locating brackets, and in this manner float-mounts the CT scanner with the SPECT scanner and facilitates the taking of the CT scan and a SPECT scan of a patient in a single-pass diagnostic procedure.

20 Claims, 9 Drawing Sheets

62,64

RELEASABLY INTERCONNECTED CT AND SPECT SCANNERS

BACKGROUND OF THE INVENTION

1. Field of the Invention

The present invention relates to systems and methods used in radiation imaging; and more particularly, to a linked combination of a CT scanner and a SPECT scanner for producing substantially simultaneous images from each scanner of a patient undergoing diagnostic analysis.

2. Description of the Background Art

Both Computed Tomography (CT) scanning and Single Photon Emission Computed Tomography (SPECT) scanning are well-known diagnostic tools for imaging internal portions of a patient. Conventionally, each of the two scanning procedures have been conducted independently using two separate station setups, each requiring its own scan process of the patient.

In view of desires to boost utilization of the two scanning arrangements and to economize staff and patient time, a need has been recognized for a one-pass procedure in which both scanning processes can be accomplished on the patient at substantially the same time, and preferably each of the two images will be complementary to one another for developing comprehensive internal images of the patient.

SUMMARY OF THE INVENTION

In an effort to meet the desires outlined above with respect to combined CT and SPECT scanning, the present invention has been developed, and in at least in one aspect, is directed toward a float connection for interconnecting a CT scanner and a SPECT scanner. The connection includes a pair of receiving brackets that are each configured to be fixedly mounted with respect to a SPECT scanner. A pair of self-locating brackets are provided and each is configured for assuming a prescribed position relative to a respective one of the pair of receiving brackets when in snug abutment therewith. A floating connection is associated with the pair of self-locating brackets and is configured to floatingly interconnect the CT scanner with the pair of self-locating brackets for float-mounting the CT scanner with a SPECT scanner. In this manner, the taking of the CT scan and a SPECT scan of a patient is facilitated in a single-pass diagnostic procedure.

In another, but related embodiment, the invention takes the form of an arrangement for taking a CT scan and a SPECT scan of a patient in a single-pass diagnostic procedure. A SPECT scanner and a CT scanner are included. The SPECT scanner is mounted on a SPECT gantry and the CT scanner is mounted on a CT gantry. The SPECT and CT gantries are moveable with respect to one another between a mated operating configuration and a separated maintenance configuration. A pair of receiving brackets is fixedly mounted on the SPECT gantry. A pair of self-locating brackets is fixedly mounted on the CT gantry. Each of the pair of self-locating brackets is configured for assuming a prescribed position relative to a respective one of the pair of receiving brackets when in snug abutment together. A floating connection interconnects the CT scanner with the pair of self-locating brackets, and in this manner float-mounts the CT scanner with the SPECT scanner and facilitates the taking of the CT scan and a SPECT scan of a patient in a single-pass diagnostic procedure.

In summary, the provision and utilization of a combined CT and SPECT scanner which is configured according to the teachings above facilitate radiological imaging of a patient, while at the same time increasing utilization of the required equipment and economizing the patient's and operator's time. Among other benefits, the method and arrangement of the present invention accommodates a single-pass diagnostic procedure in which both a CT scan and a SPECT scan are produced. In a further aspect, the invention provides a method and arrangement for connecting, disconnecting and reconnecting a CT scanner and a SPECT scanner into the same combined configuration. That is to say, the interconnection assembly of the invention facilitates the establishment of the same mated-together configuration each time after the two scanners have being separated from one another. This interconnection of the two scanners into a serial arrangement also permits the production of complementary images from each of the scanners of a scanned patient. In other words, the images from each of the two scanners can be overlaid upon one another (brought into registration with one another) thereby producing a composite or similarly enhanced image because of the manner in which the two scanners are interconnected together utilizing the method and arrangements of the present invention.

BRIEF DESCRIPTION OF THE DRAWINGS

The invention as described herein can be best appreciated and understood when taken in conjunction with the accompanying drawings, in which.

DETAILED DESCRIPTION OF THE PREFERRED EMBODIMENTS

Figure 1:
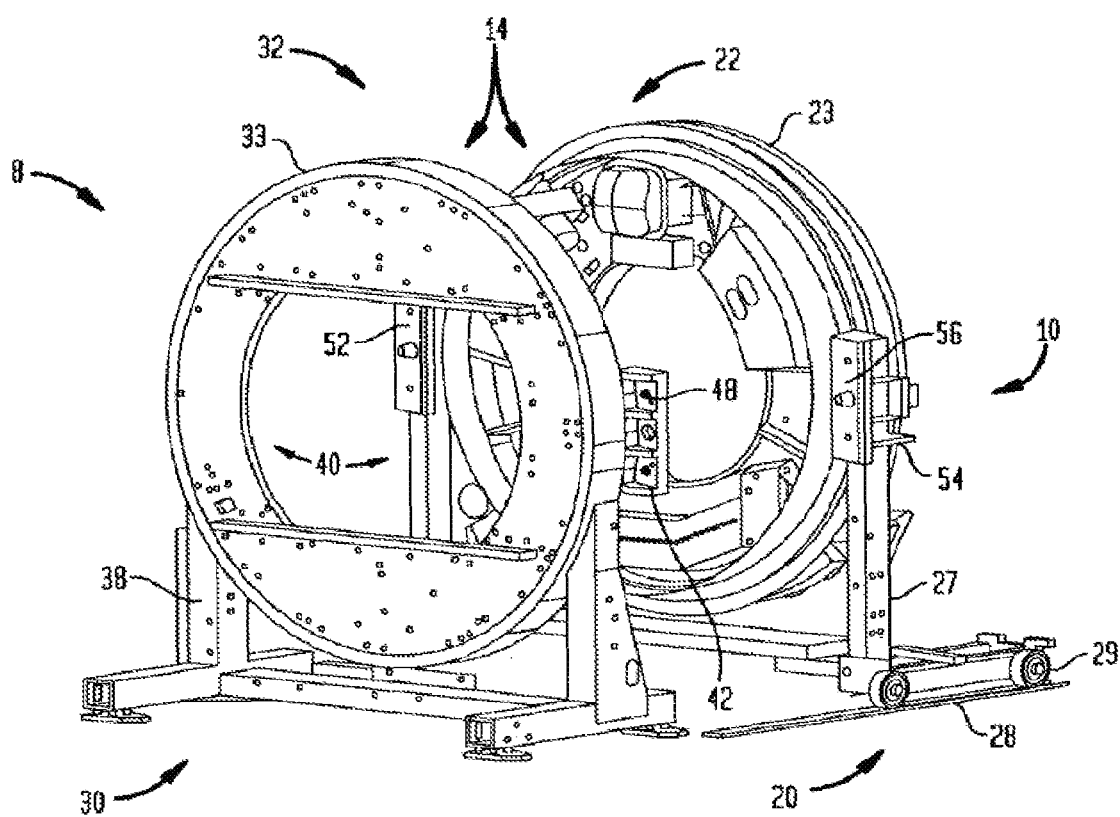
FIG. 1 is a perspective view of a SPECT scanning arrangement (in the foreground) and a CT scanning arrangement (in the background) in a separated maintenance configuration.
Figure 2:
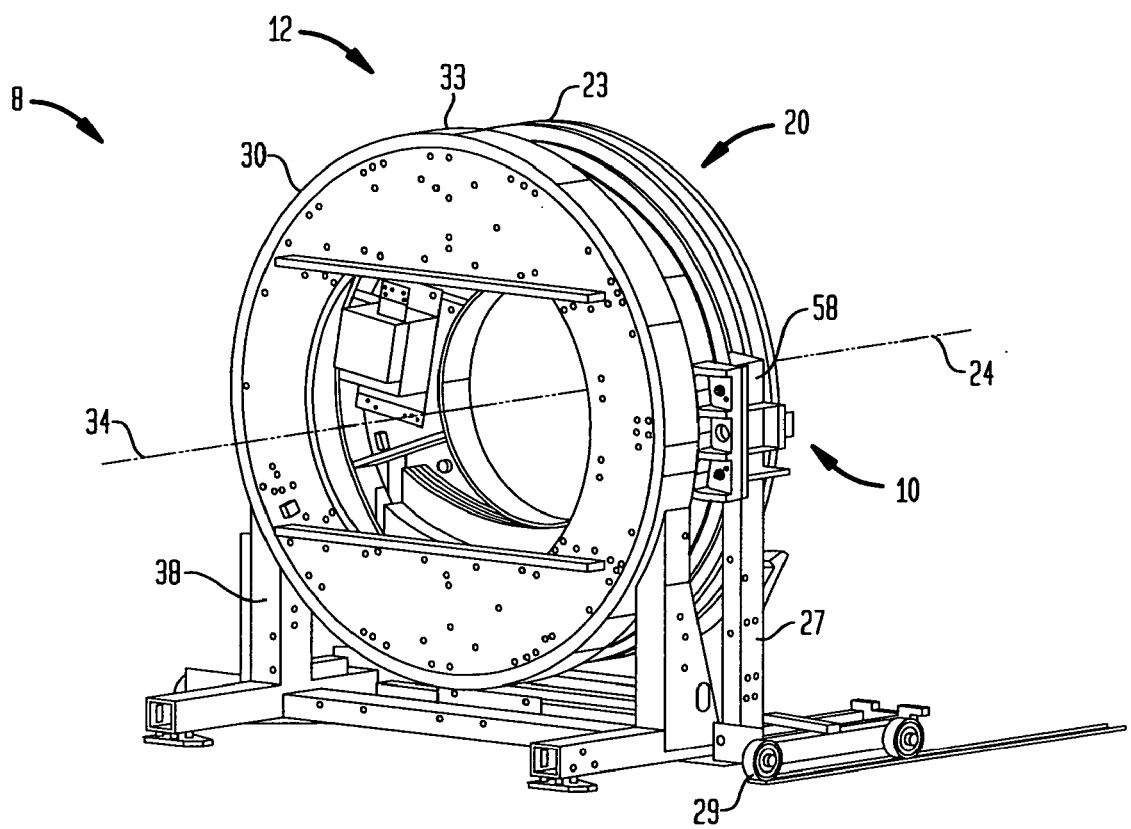
FIG. 2 is a perspective view of the SPECT and CT scanning arrangements in a mated operating configuration.

Referring to FIGS. 1 and 2, one embodiment of the invention is shown in the form of a combination arrangement (8) for taking a CT scan and a SPECT scan of a patient in a single-pass diagnostic procedure. A SPECT arrangement (30), including a SPECT scanner (32), and a CT arrangement (20), including a CT scanner (22) are interconnected by a float connection assembly (10) into the combination arrangement (8). In the present context, it should be appreciated that the terminology connected is utilized to signify to components which are connected or coupled to each other, but not necessarily directly attached.

The SPECT scanner (32) is carried within a SPECT support ring (33) for rotation about a patient. Similarly, the CT scanner (22) is carried within a CT support ring (23) also for rotation about the patient.

The SPECT scanner (32) is mounted on a SPECT gantry (38) and the CT scanner (22) is mounted on a CT gantry (27). The SPECT and CT gantries (38, 27) are moveable with respect to one another between a mated operating configuration (12) as shown in FIG. 2, and a separated maintenance configuration (14) as shown in FIG. 1.

Figure 3:
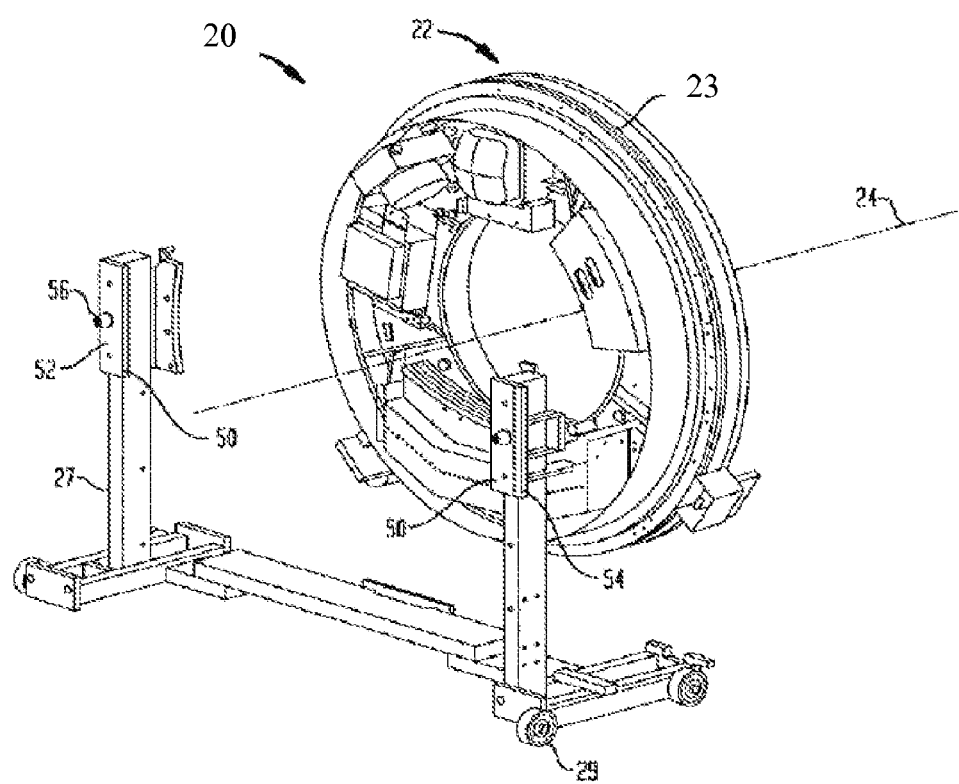
FIG. 3 is a perspective view, taken from the position of the SPECT scanning arrangement, of a CT scanning arrangement spaced apart from its supporting gantry.
Figure 4:
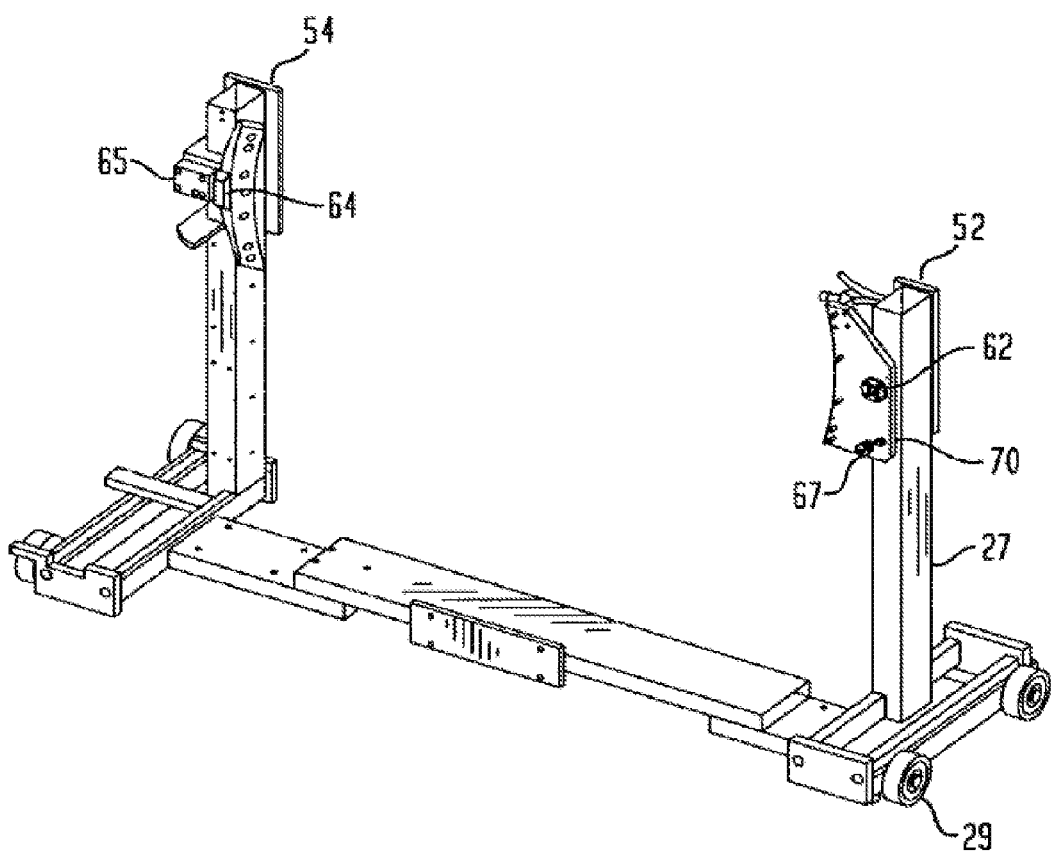
FIG. 4 is a backside perspective view of the CT-supporting gantry.

As shown in FIG. 4, a pair of receiving brackets (40) comprising a first receiving bracket (42) is fixedly mounted on the CT gantry (27). As shown in FIG. 3, pair of self-locating brackets (50) is fixedly mounted on the CT gantry (27). Each of the pair of self-locating brackets (50) is configured for assuming a prescribed position relative to a respective one of the pair of receiving brackets (60) when in snug abutment together.

A floating connection (10) interconnects the CT scanner (22) with the pair of self-locating brackets (50), and in this manner float-mounts the CT scanner (22) with the SPECT scanner (32) and facilitates the taking of the CT scan and a SPECT scan of a patient in a single-pass diagnostic procedure. More particularly, the floating connection (10) supports the CT support ring (23) in isolation thereby preventing unwanted forces from being imposed on the CT support ring (23).

In this regard, CT arrangements are known for their sensitivity to external forces. It is also known that the SPECT support ring (33) does not remain round during rotation due to the large weight of the detectors and collimators. Deviations of one-half millimeter can be expected, and as a result, direct connection of the two scanner support arrangements would have detrimental deforming affect on one another.

Figure 8:
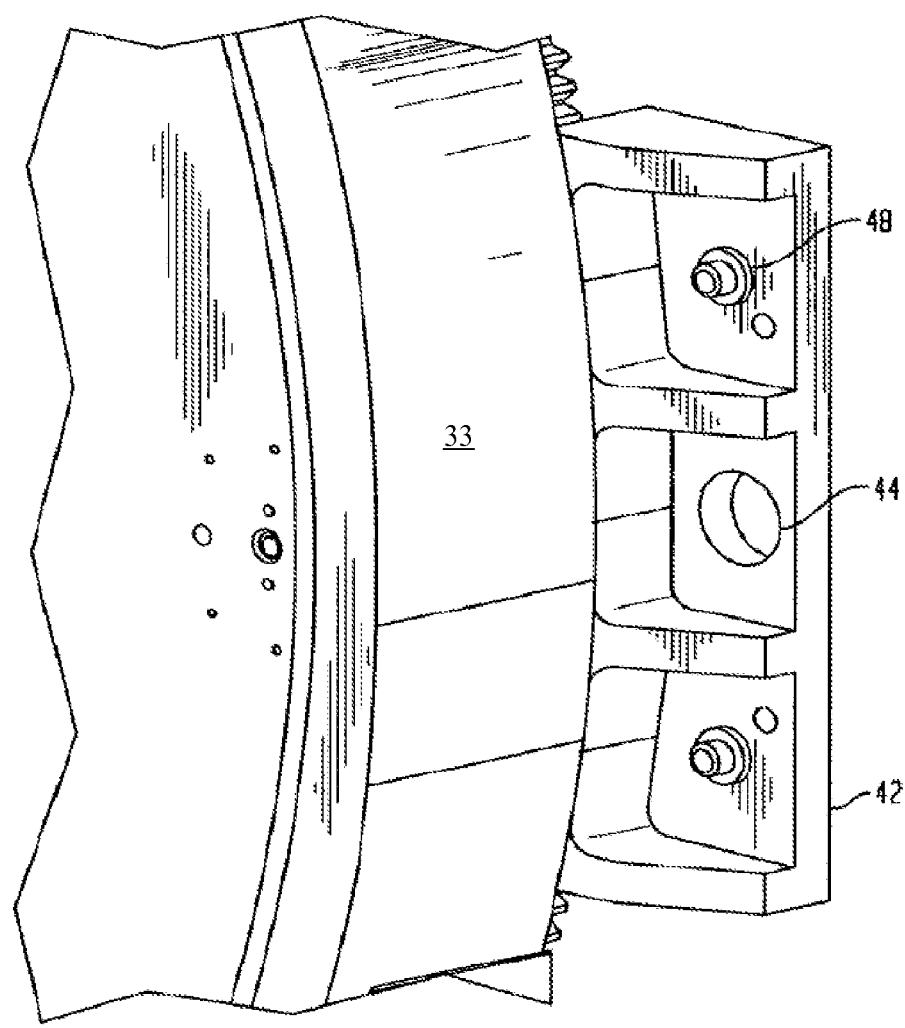
FIG. 8 is a detailed perspective view of a receiving bracket that contains a cylindrical aperture for receiving a tapered locating pin on a mating self-locating bracket of the pair.
Figure 9:
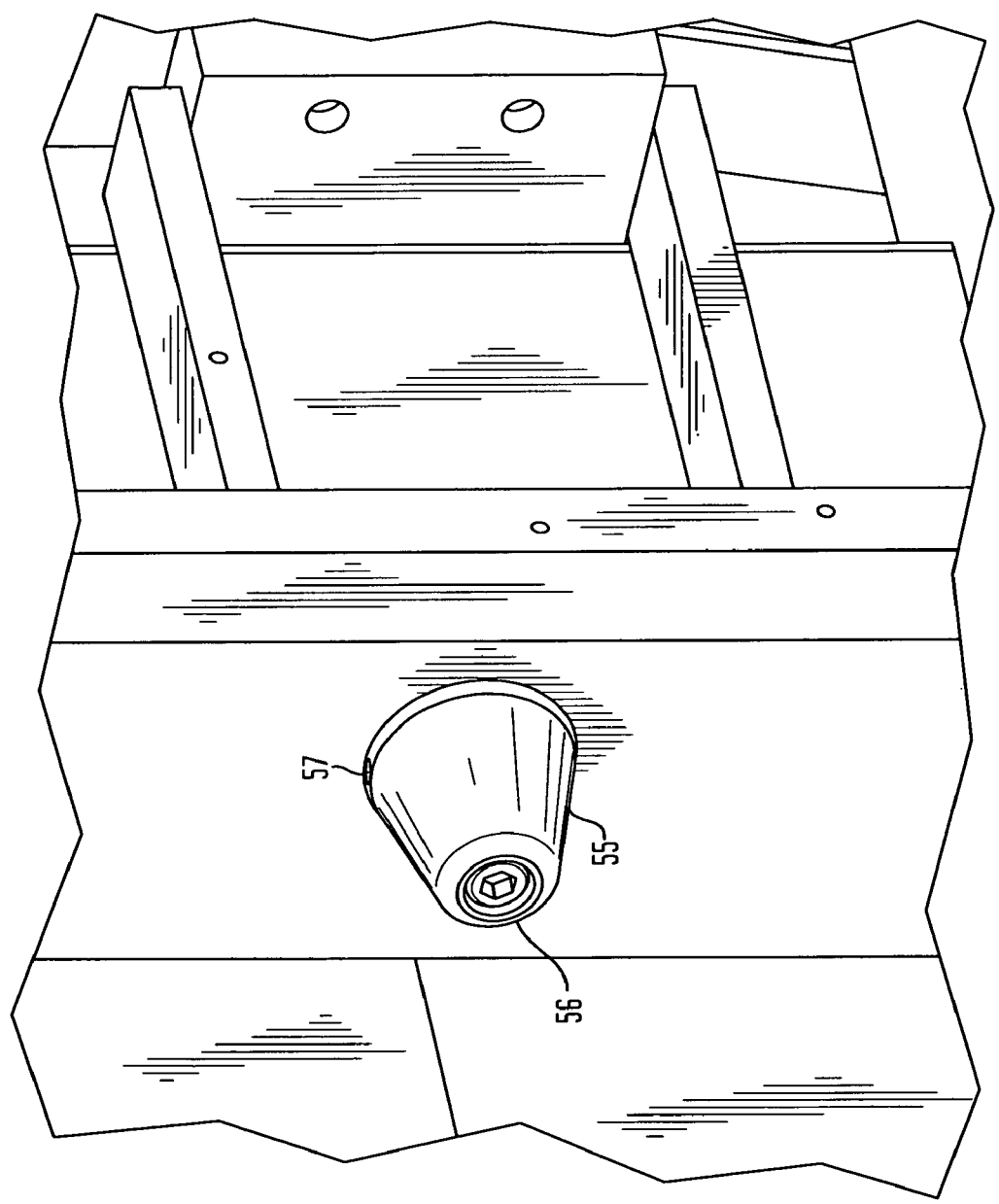
FIG. 9 is a detailed perspective view of a self-locating bracket that contains the tapered locating pin that is insertably received in the cylindrical aperture of FIG. 8.

As illustrated in FIG. 1, at least one (42) of the pair of receiving brackets (40) has a cylindrical aperture (44) for insertably receiving a tapered locating pin (56) on a respective one of the pair of self-locating brackets (50). At least one of the pair of self-locating brackets (50) has a tapered locating pin (56) for insertion into a receiving cylindrical aperture (44) in a respective one of the pair of receiving brackets (40) as shown in FIG. 3. The tapered pin (56) has a tapered portion (55) a base or root (57) that is cylindrical in shape and is configured (sized and shaped) to establish a conformance fit within the cylindrical aperture (44) of the opposite receiving bracket (42) when fully seated therein (see FIGS. 8 and 9). The close tolerance fit between the cylindrical apertures (44) and the tapered locating pins (56) ensures precise repeatability each time the gantries are rejoined thereby assuring that complementary images can be produced from each of the two linked scanners. When attachment bolts (48) are tightened, the mutual tapers cause the CT arrangement (20) to be slightly lifted, for example, on the order of one to two millimeters. This prevents the support floor from exerting any undesirable forces on the CT arrangement (20) due to settling over time.

The SPECT gantry (38) is stationarily anchored. In the illustrated embodiment, such anchorage is to the floor upon which the gantry (38) rests. The CT gantry (27) is roller-mounted for movement toward and away from the SPECT gantry (38) between the mated operating configuration (12) and the separated maintenance configuration (14). The CT gantry (27) is carried upon rollers (29) that preferably operate within tracks or floor guides (28); particularly, if the combination arrangement (8) is located on a non-rigid surface.

In a preferred embodiment, the CT gantry (27) is lifted and exclusively supported, at an off-ground position, on the pair of self-locating brackets (50) in the mated operating configuration (12). After the CT arrangement (20) has been slightly raised, the tracks or floor guides (28) can be slid out from under the rollers (29) for separate storage, thus eliminating a floor obstruction and trip hazard.

The pair of self-locating brackets (50) and the pair of receiving brackets (40) constitute a lift means (58) that raises the CT gantry (27) upon transition from the separated maintenance configuration (14) to the mated operating configuration (12).

A first spherical bearing (62) is interconnected between a first (52) of the pair of self-locating brackets (50) and the CT scanner (22). The first spherical bearing (62) permits rotation of the CT scanner (22) relative to the self-locating bracket (52) in three dimensions defined by a x-axis (16), an y-axis (18) and a z-axis (19), the x-axis (16) being substantially horizontal, the y-axis (18) being substantially vertical and the z-axis (19) being substantially parallel to a central axis (24) of the CT scanner and a central axis (34) of the SPECT scanner.

Figure 5:
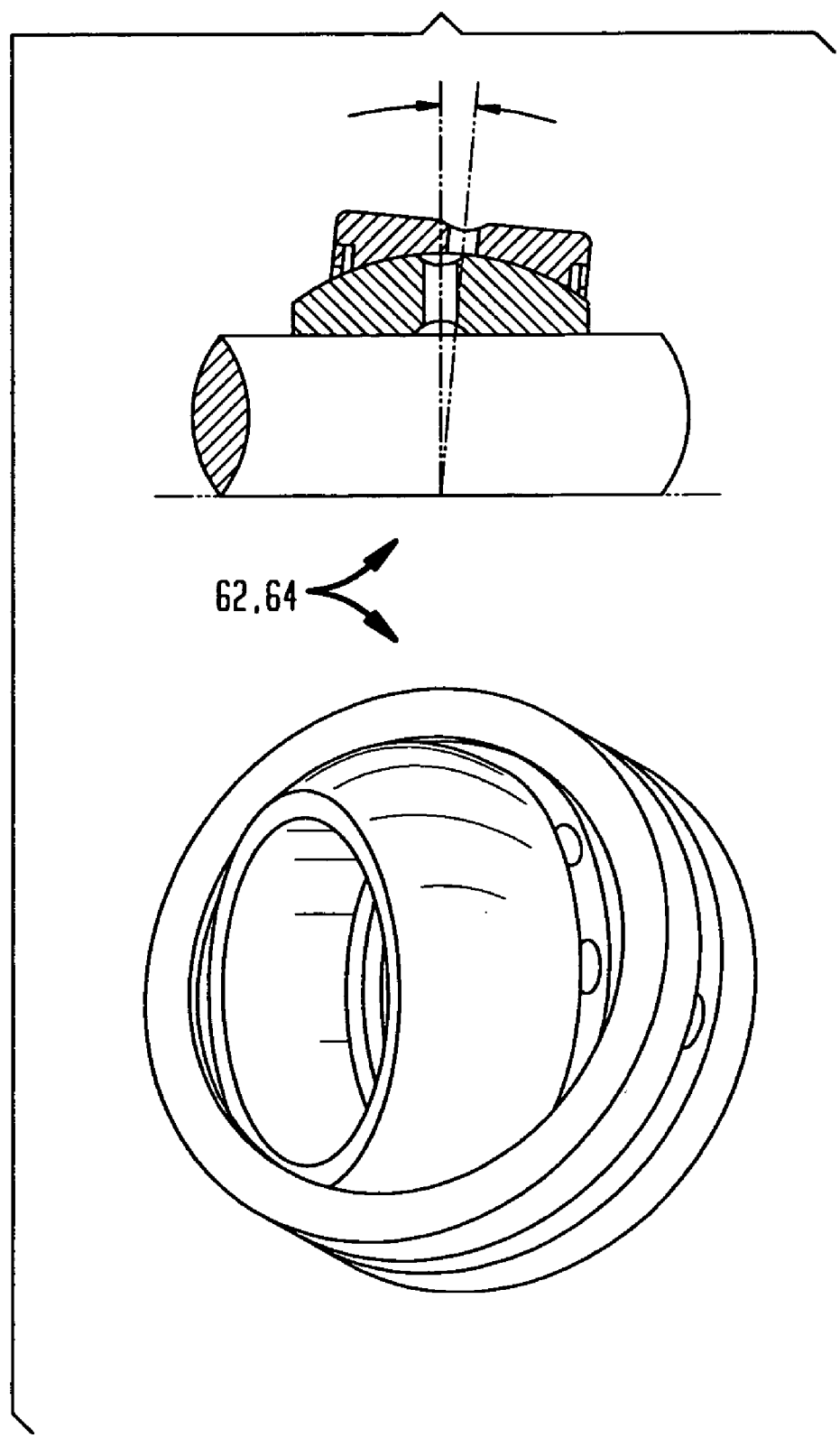
FIG. 5 is a detailed perspective view of a spherical bearing.
Figure 6:
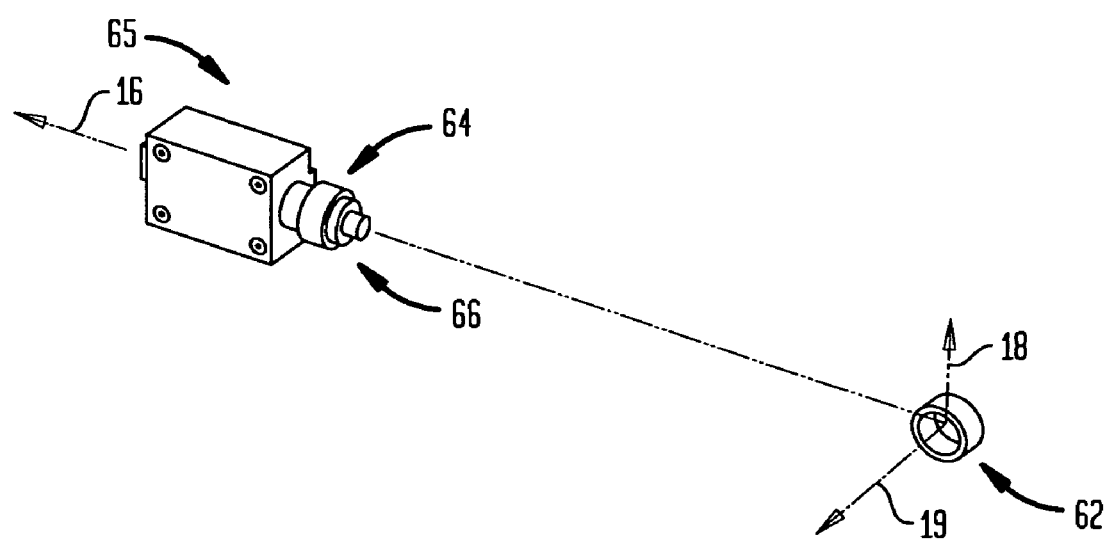
FIG. 6 is a perspective view of two spherical bearings, and in which one is mounted for linear translation.

As may be best appreciated in FIGS. 4 and 6, a second spherical bearing (64) is interconnected between a second (54) of the pair of self-locating brackets (50) and the CT scanner (22). Together with an insert pin (66) that locates in the CT support ring 23, the second spherical bearing (64) permits rotation of the CT scanner (22) relative to the x-axis (16), and prevents, in conjunction with the first spherical bearing (62), rotation of the CT scanner (22) relative to the y-axis (18) and the z-axis (19). Examples of suitable spherical bearings (62, 64) which are commercially available are depicted and FIG. 5.

The second spherical bearing (64) is mounted for linear movement in parallel with the x-axis (16) under the motivation of a translational mover 65.

A biasing element (67) is interconnected between at least one (54) of the pair of self-locating brackets (50) and the CT scanner (22) for urging rotation of the CT scanner (22) in a direction toward an adjustment device (70). The biasing element (67) and the adjustment device (70) together align the central axis (24) of the CT scanner (22) into a parallel orientation with the central axis (34) of the SPECT scanner (32).

Figure 7:
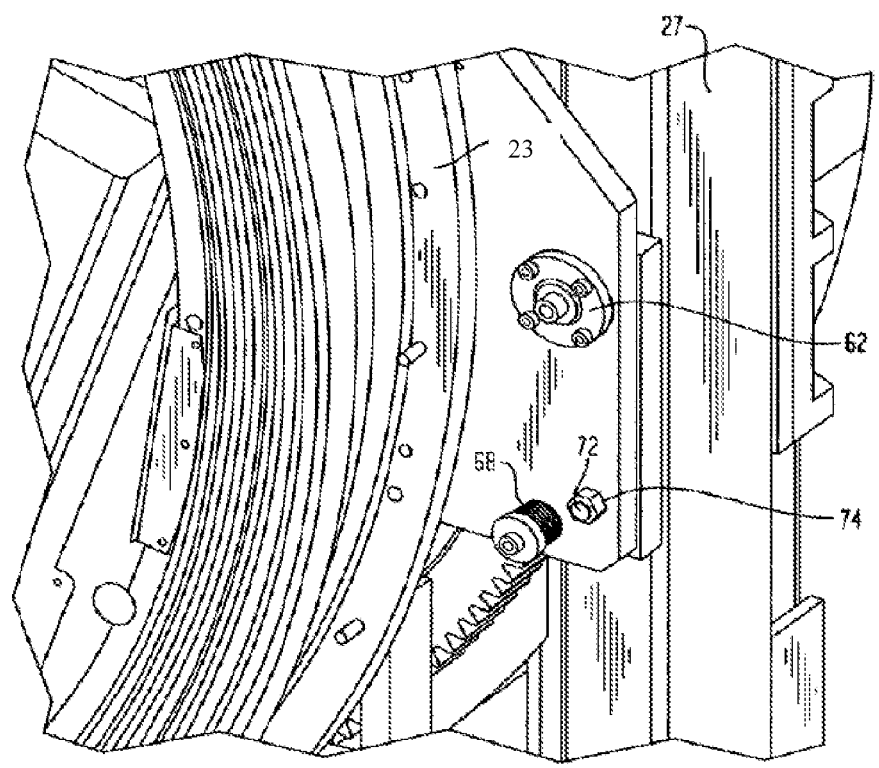
FIG. 7 is a detailed perspective view of one-half of a spherical bearing positioned above a biasing arrangement for the CT scanner.

FIG. 7 demonstrates that the biasing element (67) can exemplarily take the form of a compression spring (68) and the adjustment device (70) can exemplarily take the form of an adjustment screw (72) that is secured by a locknut (74) to a respective one (54) of the pair of self-locating brackets (50). By moving the adjustment screw (72) in and out, the orientation of the X-Y defined central planes of the scanners (22, 32) is likewise adjusted, and particularly into a desired parallel and substantially vertical orientation.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A float connection for interconnecting a CT scanner and a SPECT scanner, said connection comprising:
   a pair of receiving brackets, each configured to be fixedly mounted with respect to a SPECT scanner;

a pair of self-locating brackets, each configured for assuming a prescribed position relative to a respective one of said pair of receiving brackets when in snug abutment therewith; and a floating connection associated with said pair of self-locating brackets, said floating connection configured to floatingly interconnect a CT scanner with said pair of self-locating brackets for float-mounting the CT scanner with a SPECT scanner and thereby facilitating the taking of a CT scan and a SPECT scan of a patient in a single-pass diagnostic procedure.

2. The float connection as recited in claim 1, wherein at least one of said pair of receiving brackets has a cylindrical aperture for insertably receiving a tapered locating pin on a respective one of said pair of self-locating brackets.

3. The float connection as recited in claim 1, wherein each of said pair of receiving brackets has a cylindrical aperture for insertably receiving a tapered locating pin on a respective one of said pair of self-locating brackets.

4. The float connection as recited in claim 1, wherein at least one of said pair of self-locating brackets has a tapered locating pin for insertion into a receiving cylindrical aperture in a respective one of said pair of receiving brackets.

5. The float connection as recited in claim 1, wherein each of said pair of self-locating brackets has a tapered locating pin for insertion into a receiving cylindrical aperture in a respective one of said pair of receiving brackets.

6. The float connection as recited in claim 1, further comprising:

a spherical bearing interconnectable between a first of said pair of self-locating brackets and the CT scanner, said spherical bearing configured to permit rotation of the CT scanner relative to said self-locating bracket in three dimensions defined by a x-axis, an y-axis and a z-axis, said x-axis being substantially horizontal, said y-axis being substantially vertical and said z-axis being substantially parallel to a central axes of the CT scanner and the SPECT scanner.

7. The float connection as recited in claim 1, further comprising:

a first spherical bearing interconnectable between a first of said pair of self-locating brackets and a CT scanner, said first spherical bearing configured to permit rotation of the CT scanner relative to said self-locating bracket in three dimensions defined by a x-axis, an y-axis and a z-axis, said x-axis being substantially horizontal, said y-axis being substantially vertical and said z-axis being substantially parallel to a central axes of the CT scanner and the SPECT scanner; and a second spherical bearing interconnectable between a second of said pair of self-locating brackets and the CT scanner, said second spherical bearing configured to permit rotation of the CT scanner relative to the x-axis, and prevent, in conjunction with said first spherical bearing, rotation of the CT scanner relative to the y-axis and the z-axis.

8. The float connection as recited in claim 7, wherein said second spherical bearing is mounted for substantially linear movement in parallel with the x-axis.

9. The float connection as recited in claim 7, further comprising:

a biasing element arranged between at least one of said pair of self-locating brackets and the CT scanner for urging rotation of the CT scanner in a direction toward an adjustment device, said biasing element and said adjustment device together being configurable to align the central axis of the CT scanner into a parallel orientation with the central axis of the SPECT scanner.

10. The float connection as recited in claim 9, wherein said biasing element is a compression spring and said adjustment device is an adjustment screw secured by a locknut to a respective one of said pair of self-locating brackets.

11. An arrangement for taking a CT scan and a SPECT scan of a patient in a single-pass diagnostic procedure, said arrangement comprising:

a SPECT scanner and a CT scanner, said SPECT scanner mounted on a SPECT gantry and said CT scanner mounted on a CT gantry, said SPECT and CT gantries being moveable with respect to the other between a mated operating configuration and a separated maintenance configuration;

a pair of receiving brackets fixedly mounted on said SPECT gantry;

a pair of self-locating brackets fixedly mounted on said CT gantry, each of said pair of self-locating brackets configured for assuming a prescribed position relative to a respective one of said pair of receiving brackets when in snug abutment therewith; and a floating connection interconnecting said CT scanner with said pair of self-locating brackets and thereby float-mounting said CT scanner with said SPECT scanner and facilitating the taking of the CT scan and a SPECT scan of a patient in a single-pass diagnostic procedure.

12. The arrangement as recited in claim 11, wherein at least one of said pair of receiving brackets has a cylindrical aperture for insertably receiving a tapered locating pin on a respective one of said pair of self-locating brackets and wherein at least one of said pair of self-locating brackets has a tapered locating pin for insertion into a receiving cylindrical aperture in a respective one of said pair of receiving brackets.

13. The arrangement as recited in claim 12, wherein said SPECT gantry is stationarily anchored and said CT gantry is roller-mounted for movement toward and away from said CT gantry between said mated operating configuration and said separated maintenance configuration.

14. The arrangement as recited in claim 13, wherein said CT gantry is exclusively supported, at an off-ground position, on said self-locating brackets in the mated operating configuration.

15. The arrangement as recited in claim 13, wherein said pair of self-locating brackets and said pair of receiving brackets constitute a lift means that raises said CT gantry upon transition from said separated maintenance configuration to said mated operating configuration.

16. The arrangement as recited in claim 11, further comprising:

a spherical bearing interconnected between a first of said pair of self-locating brackets and the CT scanner, said spherical bearing permitting rotation of the CT scanner relative to said self-locating bracket in three dimensions defined by a x-axis, an y-axis and a z-axis, said x-axis being substantially horizontal, said y-axis being substantially vertical and said z-axis being substantially parallel to a central axes of the CT scanner and the SPECT scanner.

17. The arrangement as recited in claim 11, further comprising:

a first spherical bearing interconnected between a first of said pair of self-locating brackets and the CT scanner, said first spherical bearing permitting rotation of the CT scanner relative to said self-locating bracket in three dimensions defined by a x-axis, an y-axis and a z-axis, said x-axis being substantially horizontal, said y-axis being substantially vertical and said z-axis being substantially parallel to a central axes of the CT scanner and the SPECT scanner; and a second spherical bearing interconnected between a second of said pair of self-locating brackets and the CT scanner, said second spherical bearing permitting rotation of the CT scanner relative to the x-axis, and preventing, in conjunction with said first spherical bearing, rotation of the CT scanner relative to the y-axis and the z-axis.

18. The arrangement as recited in claim 17, wherein said second spherical bearing is mounted for translational movement in parallel with the x-axis.

19. The arrangement as recited in claim 17, further comprising:

a biasing element interconnected between at least one of said pair of self-locating brackets and the CT scanner for urging rotation of the CT scanner in a direction toward an adjustment device, said biasing element and said adjustment device together aligning the central axis of the CT scanner into a parallel orientation with the central axis of the SPECT scanner.

20. The arrangement as recited in claim 19, wherein said biasing element is a compression spring and said adjustment device is an adjustment screw secured by a locknut to a respective one of said pair of self-locating brackets.

\* \* \* \* \*